US010695566B1

(12) United States Patent
Kim et al.

(10) Patent No.: US 10,695,566 B1
(45) Date of Patent: Jun. 30, 2020

(54) MULTICHANNEL STIMULATION SYSTEM FOR REGENERATING DAMAGED CORNEAL NERVES

(71) Applicant: NU EYNE CO., LTD., Seoul (KR)

(72) Inventors: Do-Hyoung Kim, Seoul (KR); Pyung-Kyu Kim, Seoul (KR); Joo-Wan Seo, Seoul (KR); Won-Jang Lee, Daejeon (KR)

(73) Assignee: NU EYNE CO., LTD., Seoul (KR)

( * ) Notice: Subject to any disclaimer, the term of this patent is extended or adjusted under 35 U.S.C. 154(b) by 0 days.

(21) Appl. No.: 16/742,140

(22) Filed: Jan. 14, 2020

(30) Foreign Application Priority Data

Apr. 16, 2019 (KR) .................. 10-2019-0044505

(51) Int. Cl.
*A61N 1/04* (2006.01)
*A61N 1/36* (2006.01)
*H03K 17/567* (2006.01)

(52) U.S. Cl.
CPC ....... *A61N 1/36046* (2013.01); *A61N 1/0484* (2013.01); *A61N 1/36125* (2013.01); *H03K 17/567* (2013.01)

(58) Field of Classification Search
CPC .............. A61N 1/36046; A61N 1/0484; A61N 1/36125; H03K 17/567
See application file for complete search history.

(56) References Cited

U.S. PATENT DOCUMENTS

2018/0000639 A1* 1/2018 Alster .................. A61F 9/008

FOREIGN PATENT DOCUMENTS

| JP | H07142872 | 6/1995 |
|---|---|---|
| KR | 20170132236 | 12/2017 |
| KR | 20180125997 | 11/2018 |
| WO | WO2017/048731 | 3/2017 |

* cited by examiner

*Primary Examiner* — George Manuel
(74) *Attorney, Agent, or Firm* — IPLA P.A.; James E. Bame

(57) ABSTRACT

A multichannel stimulation system for regenerating damaged corneal nerves, includes: a multichannel unit including a first channel formed of a conductive material and attached between an area above a left eye and a left eyebrow to transfer a stimulation signal, and a second channel formed of a conductive material and attached between an area above a right eye and a right eyebrow to transfer the stimulation signal; and a stimulation signal module for providing the first channel and the second channel with an electric pulse signal as the stimulation signal, wherein the multichannel unit includes a contactor formed between the first channel and the second channel in one piece to electrically contact with the stimulation signal module.

22 Claims, 8 Drawing Sheets

US 10,695,566 B1

MULTICHANNEL STIMULATION SYSTEM FOR REGENERATING DAMAGED CORNEAL NERVES

CROSS REFERENCE

The present application claims priority to Korean Patent Application No. 10-2019-0044505, filed 16 Apr. 2019, the entire contents of which is incorporated herein by its entirety.

BACKGROUND

The present invention relates to a multichannel stimulation system for regenerating damaged corneal nerves, and more specifically, to a multichannel stimulation system for regenerating damaged corneal nerves, which can effectively regenerate damaged corneal nerves by applying electric pulse signal as a stimulation signal through multiple channels attached in a plurality of areas close to the eyes.

After the permission of Food and Drug Administration (FDA) in the mid-1990s, about 30 million people worldwide have undergone vision correction surgery for myopia treatment, and recently in Korea, more than half of the population needs vision correction surgery as a result of aging population and rapid increase in the use of digital devices.

Accordingly, it is estimated that more than 200,000 people undergo laser vision correction surgery every year in Korea, and this laser vision correction surgery damages the corneal nerve bundles in the process of physically affecting the corneal epithelium to correct refractive error.

The density and sensory function of the actual corneal nerve bundles tend to decrease immediately after the laser vision correction surgery, and it has been found that dry eye syndrome and corneal pain, which are frequent side effects of the laser vision correction surgery, are closely related to the corneal nerve bundles.

Recently, thanks to the rapid development of neuromodulation and research of nervous system, understanding of the growth and function of nerve cells is increasing. In addition, according to the accumulated technologies, it is shown that nerve regeneration may control activities by means of inherent features and regeneration of nerves and tissues can be accelerated by using minute electrical stimulation in regenerating peripheral nerves.

Accordingly, although various methods are proposed to treat patients suffering from visual disorder using minute electrical stimulation, effective treatment is difficult as the methods simply exercise electrical stimulation through probes.

The background technology of the present invention is disclosed in Korean Laid-opened Patent No. 10-2018-0125997 released on Nov. 26, 2018.

SUMMARY OF THE INVENTION

Therefore, the present invention has been made in view of the above problems, and it is an object of the present invention to provide a multichannel stimulation system for regenerating damaged corneal nerves, which can effectively regenerate damaged corneal nerves by applying an electric pulse signal as stimulation signal through multiple channels attached in a plurality of areas close to the eyes.

The technical problems to be solved by the present invention are not limited to the technical problems mentioned above, and unmentioned other technical problems may be clearly understood by those skilled in the art from the following descriptions.

To accomplish the above object, according to an embodiment of the present invention, there is provided a multichannel stimulation system for regenerating damaged corneal nerves, the system comprising: a multichannel unit including a first channel formed of a conductive material and attached between an area above the left eye and the left eyebrow to transfer a stimulation signal, and a second channel formed of a conductive material and attached between an area above the right eye and the right eyebrow to transfer the stimulation signal; and a stimulation signal module for providing the first channel and the second channel with an electric pulse signal as the stimulation signal, wherein the multichannel unit includes a contactor formed between the first channel and the second channel in one piece to electrically contact with the stimulation signal module, and the electric pulse signal is configured of a positive current electric pulse signal during a first duration time, a zero current electric pulse signal during a second duration time following the first duration time, a negative current pulse signal during a third duration time following the second duration time, a zero current electric pulse signal during a fourth duration time following the third duration time, a negative current electric pulse signal during a fifth duration time following the fourth duration time, a zero current electric pulse signal during a sixth duration time following the fifth duration time, a positive current electric pulse signal during a seventh duration time following the sixth duration time, and a zero current electric pulse signal during an eighth duration time following the seventh duration time, and the length of the first duration time of the electric pulse signal is 2 to 15 times of the length of the third duration time of the electric pulse signal, and the length of the fifth duration time of the electric pulse signal is 2 to 15 times of the length of the seventh duration time of the electric pulse signal.

In the multichannel stimulation system for regenerating damaged corneal nerves according to an embodiment of the present invention, a magnet is arranged in each of the contactor of the multichannel unit and the stimulation signal module, and when the contactor of the multichannel unit and the stimulation signal module approach each other within a predetermined range, the contactor of the multichannel unit and the stimulation signal module may be self-aligned by the attraction force of the arranged magnets.

In the multichannel stimulation system for regenerating damaged corneal nerves according to an embodiment of the present invention, when a pressure is applied to an up button of the stimulation signal module, the magnitude of the electric pulse signal may be increased in proportion to the number of times of applying the pressure to the up button, and when a pressure is applied to the down button of the stimulation signal module, the magnitude of the electric pulse signal may be decreased in inverse proportion to the number of times of applying the pressure to the down button.

In the multichannel stimulation system for regenerating damaged corneal nerves according to an embodiment of the present invention, when a pressure is applied to the up button, the stimulation signal module may control to increase the magnitude of the electric pulse signal by adjusting the number of pulses of a pulse width modulation signal in proportion to the number of times of applying the pressure to the up button, and when a pressure is applied to the down button, the stimulation signal module may control to decrease the magnitude of the electric pulse signal by adjusting the number of pulses of the pulse width modulation signal in inverse proportion to the number of times of applying the pressure to the down button.

In the multichannel stimulation system for regenerating damaged corneal nerves according to an embodiment of the present invention, the fourth duration time of the electric pulse signal may be 5 to 2,000 times of the second duration time of the electric pulse signal.

In the multichannel stimulation system for regenerating damaged corneal nerves according to an embodiment of the present invention, the eighth duration time of the electric pulse signal may be 5 to 2,000 times of the sixth duration time of the electric pulse signal.

In the multichannel stimulation system for regenerating damaged corneal nerves according to an embodiment of the present invention, the magnitude of the absolute value of the positive current electric pulse signal of the first duration time of the electric pulse signal may be equal to the magnitude of the absolute value of the negative current electric pulse signal of the third duration time of the electric pulse signal, and the magnitude of the absolute value of the negative current electric pulse signal of the fifth duration time of the electric pulse signal may be equal to the magnitude of the absolute value of the positive current electric pulse signal of the seventh duration time of the electric pulse signal.

In the multichannel stimulation system for regenerating damaged corneal nerves according to an embodiment of the present invention, the magnitude of the absolute value of the positive current electric pulse signal of the first duration time of the electric pulse signal may be 2 to 15 times of the magnitude of the absolute value of the negative current electric pulse signal of the third duration time of the electric pulse signal, and the magnitude of the absolute value of the negative current electric pulse signal of the fifth duration time of the electric pulse signal may be 2 to 15 times of the magnitude of the absolute value of the positive current electric pulse signal of the seventh duration time of the electric pulse signal.

In the multichannel stimulation system for regenerating damaged corneal nerves according to an embodiment of the present invention, the electric pulse signal may be in a charge-balanced state.

In the multichannel stimulation system for regenerating damaged corneal nerves according to an embodiment of the present invention, the stimulation signal module may provide the first channel with the electric pulse signal of the first duration time and the electric pulse signal of the seventh duration time, and provide the second channel with the electric pulse signal of the third duration time and the electric pulse signal of the fifth duration time.

To accomplish the above object, according to another embodiment of the present invention, there is provided a multichannel stimulation system for regenerating damaged corneal nerves, the system comprising: a multichannel unit including a 11-th channel formed of a conductive material and attached above the left eyebrow to transfer a stimulation signal, a 12-th channel formed of a conductive material and attached below the left eye to transfer the stimulation signal, a 21-th channel formed of a conductive material and attached above the right eyebrow to transfer the stimulation signal, and a 22-th channel formed of a conductive material and attached below the right eye to transfer the stimulation signal; and a stimulation signal module for providing the 11-th channel, the 12-th channel, the 21-th channel, and the 22-th channel with an electric pulse signal as the stimulation signal, wherein the multichannel unit includes a contactor formed between the 11-th channel and the 21-th channel in one piece to electrically contact with the stimulation signal module, and the electric pulse signal is configured of a positive current pulse signal during a first duration time, a zero current electric pulse signal during a second duration time following the first duration time, a negative current pulse signal during a third duration time following the second duration time, a zero current electric pulse signal during a fourth duration time following the third duration time, a negative current pulse signal during a fifth duration time following the fourth duration time, a zero current electric pulse signal during a sixth duration time following the fifth duration time, a positive current pulse signal during a seventh duration time following the sixth duration time, and a zero current electric pulse signal during an eighth duration time following the seventh duration time, and the length of the first duration time of the electric pulse signal is 2 to 15 times of the length of the third duration time of the electric pulse signal, and the length of the fifth duration time of the electric pulse signal is 2 to 15 times of the length of the seventh duration time of the electric pulse signal.

In the multichannel stimulation system for regenerating damaged corneal nerves according to another embodiment of the present invention, a magnet is arranged in each of the contactor of the multichannel unit and the stimulation signal module, and when the contactor of the multichannel unit and the stimulation signal module approach each other within a predetermined range, the contactor of the multichannel unit and the stimulation signal module may be self-aligned by an attraction force of the arranged magnets.

In the multichannel stimulation system for regenerating damaged corneal nerves according to another embodiment of the present invention, when a pressure is applied to an up button of the stimulation signal module, the magnitude of the electric pulse signal may be increased in proportion to the number of times of applying the pressure to the up button, and when a pressure is applied to the down button of the stimulation signal module, the magnitude of the electric pulse signal may be decreased in inverse proportion to the number of times of applying the pressure to the down button.

In the multichannel stimulation system for regenerating damaged corneal nerves according to another embodiment of the present invention, when a pressure is applied to the up button, the stimulation signal module may control to increase the magnitude of the electric pulse signal by adjusting the number of pulses of a pulse width modulation signal in proportion to the number of times of applying the pressure to the up button, and when a pressure is applied to the down button, the stimulation signal module may control to decrease the magnitude of the electric pulse signal by adjusting the number of pulses of the pulse width modulation signal in inverse proportion to the number of times of applying the pressure to the down button.

In the multichannel stimulation system for regenerating damaged corneal nerves according to another embodiment of the present invention, the fourth duration time of the electric pulse signal may be 5 to 2,000 times of the second duration time of the electric pulse signal.

In the multichannel stimulation system for regenerating damaged corneal nerves according to another embodiment of the present invention, the eighth duration time of the electric pulse signal may be 5 to 2,000 times of the sixth duration time of the electric pulse signal.

In the multichannel stimulation system for regenerating damaged corneal nerves according to another embodiment of the present invention, the magnitude of the absolute value of the positive current electric pulse signal of the first duration time of the electric pulse signal may be equal to the magnitude of the absolute value of the negative current electric pulse signal of the third duration time of the electric pulse signal, and the magnitude of the absolute value of the negative current electric pulse signal of the fifth duration time of the electric pulse signal may be equal to the magnitude of the absolute value of the positive current electric pulse signal of the seventh duration time of the electric pulse signal.

In the multichannel stimulation system for regenerating damaged corneal nerves according to another embodiment of the present invention, the magnitude of the absolute value of the positive current electric pulse signal of the first duration time of the electric pulse signal may be 2 to 15 times of the magnitude of the absolute value of the negative current electric pulse signal of the third duration time of the electric pulse signal, and the magnitude of the absolute value of the negative current electric pulse signal of the fifth duration time of the electric pulse signal may be 2 to 15 times of the magnitude of the absolute value of the positive current electric pulse signal of the seventh duration time of the electric pulse signal.

In the multichannel stimulation system for regenerating damaged corneal nerves according to another embodiment of the present invention, the electric pulse signal may be in a charge-balanced state.

In the multichannel stimulation system for regenerating damaged corneal nerves according to another embodiment of the present invention, the stimulation signal module may provide the 11-th channel with the electric pulse signal of the first duration time and the electric pulse signal of the seventh duration time, provide the 12-th channel with the electric pulse signal of the third duration time and the electric pulse signal of the fifth duration time, provide the 21-th channel with the electric pulse signal of the first duration time and the electric pulse signal of the seventh duration time, and provide the 22-th channel with the electric pulse signal of the third duration time and the electric pulse signal of the fifth duration time.

DETAILED DESCRIPTION OF THE PREFERRED EMBODIMENT

Figure 1:
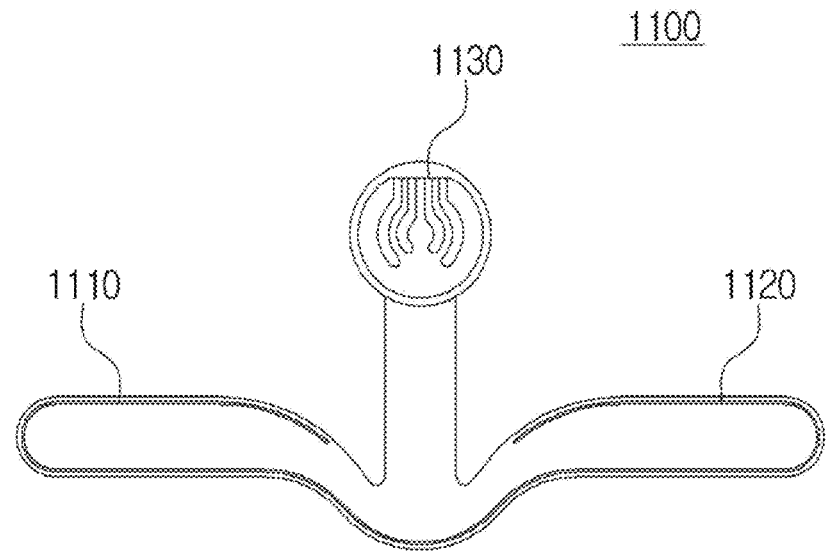
FIG. 1 is a view showing a multichannel unit of a multichannel stimulation system for regenerating damaged corneal nerves according to an embodiment of the present invention.

The detailed description of the present invention will be described below with reference to the accompanying drawings which show specific embodiments that the present invention can be embodied as an example. The embodiments are described in detail to be sufficient for those skilled in the art to embody the present invention. It should be understood that although the diverse embodiments of the present invention are different from each other, they do not need to be mutually exclusive. For example, specific shapes, structures and features described herein may be implemented as another embodiment without departing from the spirit and scope of the present invention in relation to an embodiment. In addition, it should be understood that the locations or arrangements of individual components in each disclosed embodiment may be changed without departing from the spirit and scope of the present invention.

Therefore, it is not intended to take the detailed description described below in a limited sense, and if appropriately explained, the scope of the present invention is limited only by the attached claims, together with all the scopes equivalent to the claims. Like reference numerals in the drawings denote like or similar functions throughout several aspects, and the length, area, thickness and the like and the shape may be exaggerated for convenience.

Hereinafter, a multichannel stimulation system for regenerating damaged corneal nerves according to an embodiment of the present invention will be described with reference to FIGS. 1 to 6.

Figure 2:
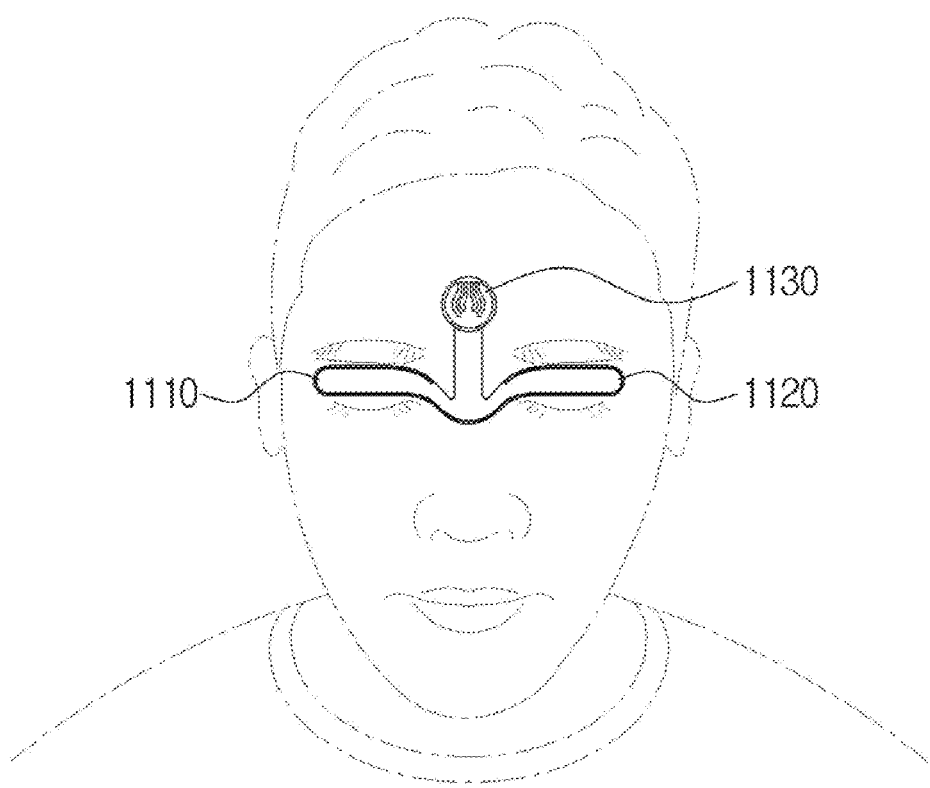
FIG. 2 is a view showing a state of attaching a multichannel unit of a multichannel stimulation system for regenerating damaged corneal nerves according to an embodiment of the present invention in an area close to the eyes of a person.
Figure 3:
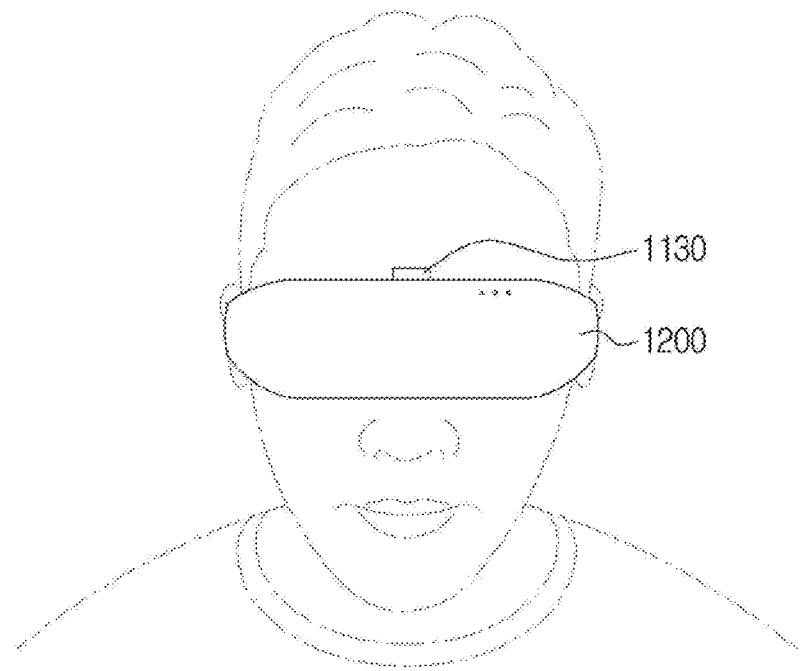
FIG. 3 is a view showing a state of attaching a multichannel unit and a stimulation signal module of a multichannel stimulation system for regenerating damaged corneal nerves according to an embodiment of the present invention in an area close to the eyes of a person.
Figure 4:
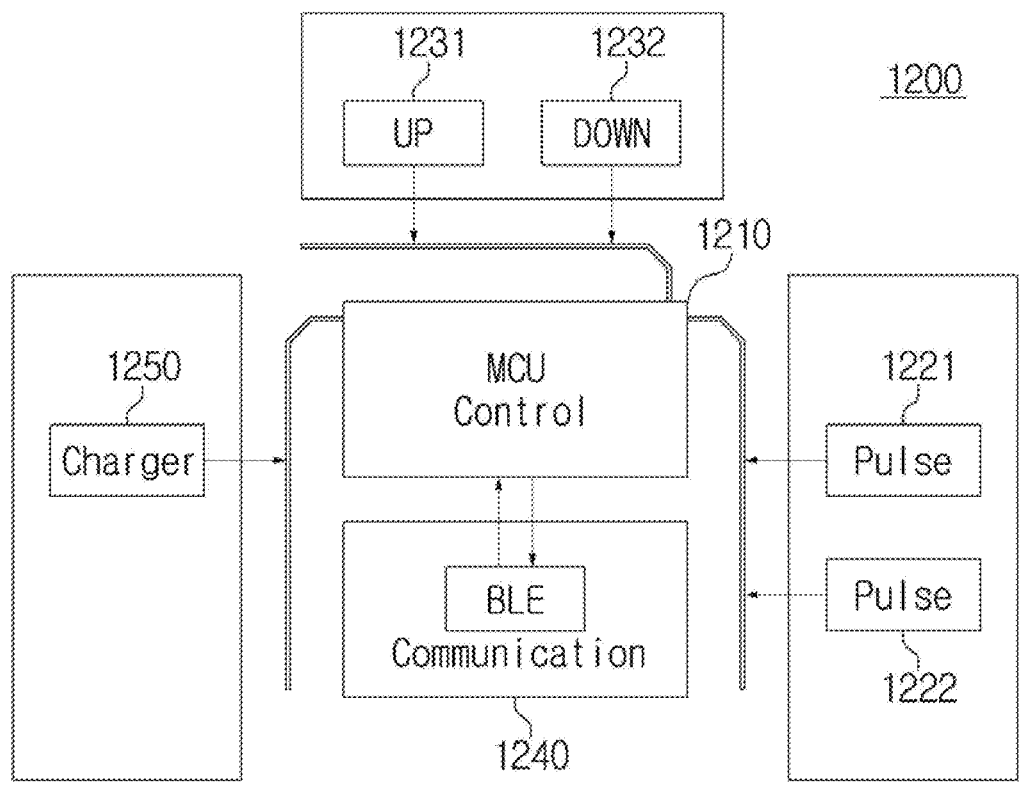
FIG. 4 is a block diagram showing a stimulation signal module of a multichannel stimulation system for regenerating damaged corneal nerves according to an embodiment of the present invention.
Figure 5:
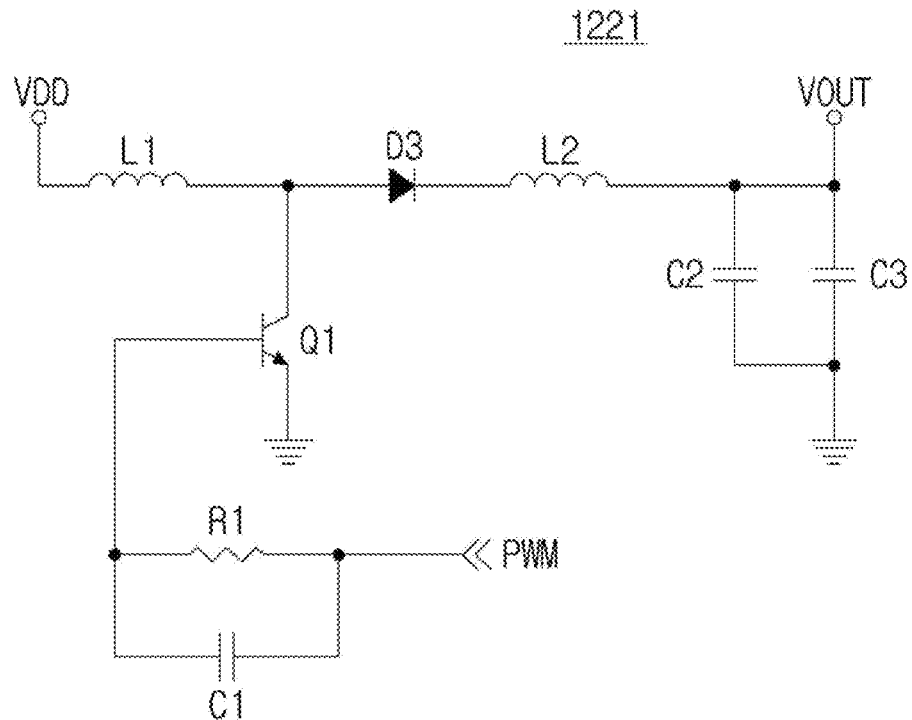
FIG. 5 is a voltage control circuit diagram according to pressure recovery of an up button or a down button employed in a stimulation signal module of a multichannel stimulation system for regenerating damaged corneal nerves according to an embodiment of the present invention.
Figure 6:
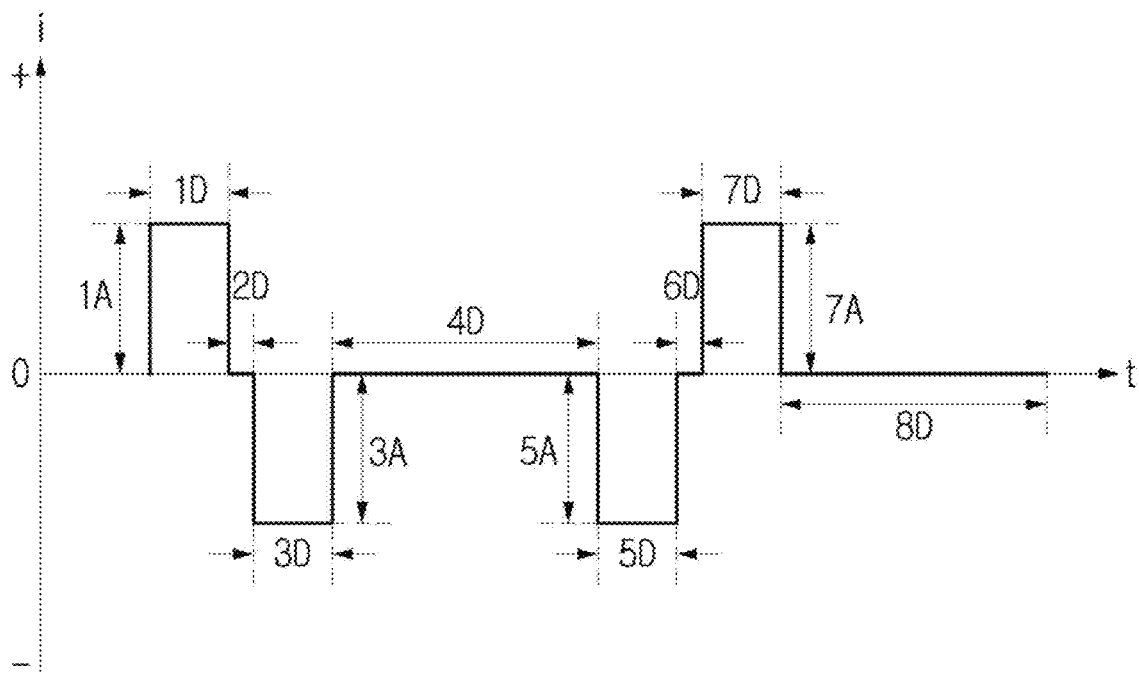
FIG. 6 is a view showing an electric pulse signal provided by a stimulation signal module of a multichannel stimulation system for regenerating damaged corneal nerves according to an embodiment of the present invention.

FIG. 1 is a view showing a multichannel unit of a multichannel stimulation system for regenerating damaged corneal nerves according to an embodiment of the present invention, FIG. 2 is a view showing a state of attaching a multichannel unit of a multichannel stimulation system for regenerating damaged corneal nerves according to an embodiment of the present invention in an area close to the eyes of a person, FIG. 3 is a view showing a state of attaching a multichannel unit and a stimulation signal module of a multichannel stimulation system for regenerating damaged corneal nerves according to an embodiment of the present invention in an area close to the eyes of a person, FIG. 4 is a block diagram showing a stimulation signal module of a multichannel stimulation system for regenerating damaged corneal nerves according to an embodiment of the present invention, FIG. 5 is a voltage control circuit diagram according to pressure recovery of an up button or a down button employed in a stimulation signal module of a multichannel stimulation system for regenerating damaged corneal nerves according to an embodiment of the present invention, and FIG. 6 is a view showing an electric pulse signal provided by a stimulation signal module of a multichannel stimulation system for regenerating damaged corneal nerves according to an embodiment of the present invention.

As shown in FIGS. 1 and 2, a multichannel unit 1100 of a multichannel stimulation system for regenerating damaged corneal nerves according to an embodiment of the present invention includes a first channel 1110 formed of a conductive material and attached between an area above the left eye and the left eyebrow to transfer a stimulation signal, a second channel 1120 formed of a conductive material and attached between an area above the right eye and the right eyebrow to transfer the stimulation signal, and a contactor 1130 formed between the first channel 1110 and the second channel 1120 in one piece to electrically contact with a stimulation signal module 1200. Here, the first channel 1110, the second channel 1120 and the contactor 1130 may be formed of Ag, AgCl, Au, Pt or stainless steel.

In addition, the stimulation signal module 1200 provides the first channel 1110 and the second channel 1120 with an electric pulse signal as the stimulation signal and may be worn between the eyes and the nose of a person like wearing goggles as shown in FIG. 3, and a magnet is arranged in each of the contactor 1130 of the multichannel unit 1100 and the stimulation signal module 1200, and when the contactor 1130 of the multichannel unit 1100 and the stimulation signal module 1200 approach each other within a predetermined range, the contactor 1130 of the multichannel unit 1100 and the stimulation signal module 1200 are self-aligned by the attraction force of the magnets.

Meanwhile, as shown in FIG. 4, the stimulation signal module 1200 described above includes stimulation signal providing units 1221 and 1222 for generating a electric pulse signal, a control unit 1210 for controlling the stimulation signal providing units 1221 and 1222, an up button 1231, a down button 1232, a communication unit 1240 communicating with the outside, and a charge unit 1250.

When a pressure is applied to the up button 1231 of the stimulation signal module 1200, the magnitude of the electric pulse signal is increased in proportion to the number of times of applying the pressure to the up button 1231, and when a pressure is applied to the down button 1232 of the stimulation signal module 1200, the magnitude of the electric pulse signal is decreased in inverse proportion to the number of times of applying the pressure to the down button 1232.

Specifically, when a pressure is applied to the up button 1231, the stimulation signal module 1200 controls to increase the magnitude of the electric pulse signal by adjusting the number of pulses of a pulse width modulation (PWM) signal in proportion to the number of times of applying the pressure to the up button 1231, and when a pressure is applied to the down button 1232, the stimulation signal module 1200 controls to decrease the magnitude of the electric pulse signal by adjusting the number of pulses of the pulse width modulation (PWM) signal in inverse proportion to the number of times of applying the pressure to the down button 1232.

For example, when the number of times of applying pressure to the up button 1231 is three, as shown in FIG. 5, three pulse width modulation (PWM) signals are transferred to the transistor Q1, and the transistor Q1 is turned on during the three pulse width modulation (PWM) signals, and therefore, the voltage boosted by the inductor L1 is charged in the capacitors C2 and C3 in proportion to the change of current which flows during the three pulse width modulation (PWM) signals. Accordingly, since the boosted voltage is charged in the capacitors C2 and C3 in proportion to the number of pulse width modulation (PWM) signals, it may be controlled to increase the magnitude of the electric pulse signal in proportion to the number of times of applying the pressure to the up button 1231 and to decrease the magnitude of the electric pulse signal in inverse proportion to the number of times of applying the pressure to the down button 1232.

As shown in FIG. 6, the electric pulse signal is configured of a positive current pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

The fourth duration time 4D of the electric pulse signal is 5 to 2,000 times of the second duration time 2D of the electric pulse signal, and the eighth duration time 8D of the electric pulse signal is 5 to 2,000 times of the sixth duration time 6D of the electric pulse signal.

For example, when the second duration time 2D of the electric pulse signal is 5 µs, the fourth duration time 4D of the electric pulse signal is 25 to 10,000 µs, and when the sixth duration time 6D of the electric pulse signal is 5 µs, the eighth duration time 8D of the electric pulse signal is 25 to 10,000 µs.

In addition, magnitude 1A of the absolute value of the positive current electric pulse signal of the first duration time 1D of the electric pulse signal is equal to magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is equal to magnitude 7A of the absolute value of the positive current electric pulse signal of the seventh duration time 7D of the electric pulse signal.

Meanwhile, magnitude 1A of the absolute value of the positive current electric pulse signal of the first duration time 1D of the electric pulse signal is 2 to 15 times of magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is 2 to 15 times of magnitude 7A of the absolute value of the positive current electric pulse signal of the seventh duration time 7D of the electric pulse signal.

For example, the electric pulse signal is configured to be in a charge-balanced state by configuring the absolute value of the positive current electric pulse signal of the first duration time 1D to be 2 to 15 mA when the absolute value of the negative current electric pulse signal of the third duration time 3D is 1 mA during the equal first duration time 1D and third duration time 3D, and the absolute value of the negative current electric pulse signal of the fifth duration time 5D to be 2 to 15 mA when the absolute value of the positive current electric pulse signal of the seventh duration time 7D is 1 mA during the equal fifth duration time 5D and seventh duration time 7D.

In addition, the length of the first duration time 1D of the electric pulse signal is equal to the length of the third duration time 3D of the electric pulse signal, and the length of the fifth duration time 5D of the electric pulse signal is equal to the length of the seventh duration time 7D of the electric pulse signal.

Meanwhile, the length of the first duration time 1D of the electric pulse signal is 2 to 15 times of the length of the third duration time 3D of the electric pulse signal, and the length of the fifth duration time 5D of the electric pulse signal is 2 to 15 times of the length of the seventh duration time 7D of the electric pulse signal.

For example, the electric pulse signal is configured to be in a charge-balanced state by configuring the first duration time 1D to be 20 to 300 μs when magnitude 1A of the absolute value of the positive current electric pulse signal of the first duration time 1D is equal to magnitude 3A of the absolute value of the negative current electric pulse signal of the third duration time 3D and the length of the third duration time 3D is 10 μs, and the fifth duration time 5D to be 20 to 300 μs when magnitude 5A of the absolute value of the negative current electric pulse signal of the fifth duration time 5D is equal to magnitude 7A of the absolute value of the positive current electric pulse signal of the seventh duration time 7D and the length of the seventh duration time 7D is 10 μs.

Meanwhile, the stimulation signal module 1200 provides the first channel 1110 with the electric pulse signal of the first duration time 1D and the electric pulse signal of the seventh duration time 7D, and provides the second channel 1120 with the electric pulse signal of the third duration time 3D and the electric pulse signal of the fifth duration time 5D.

Hereinafter, a multichannel stimulation system for regenerating damaged corneal nerves according to another embodiment of the present invention will be described with reference to FIGS. 7 to 12.

Figure 7:
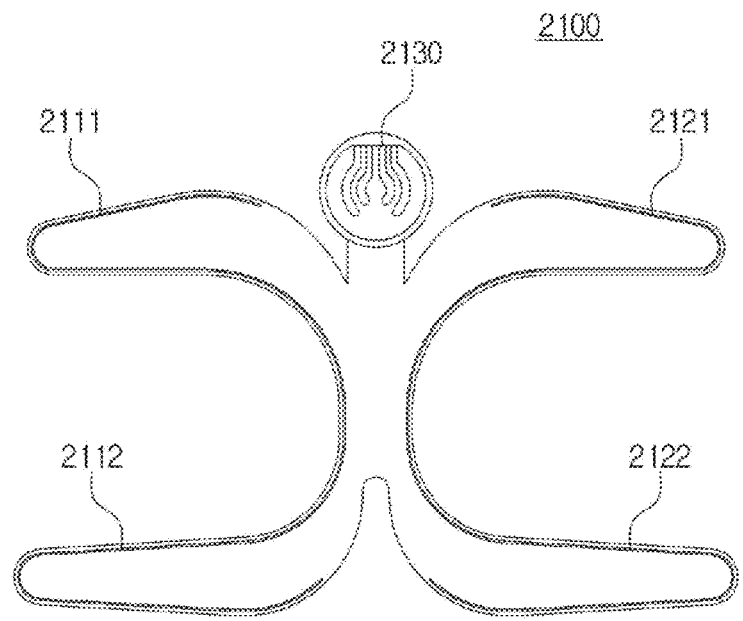
FIG. 7 is a view showing a multichannel unit of a multichannel stimulation system for regenerating damaged corneal nerves according to another embodiment of the present invention.
Figure 8:
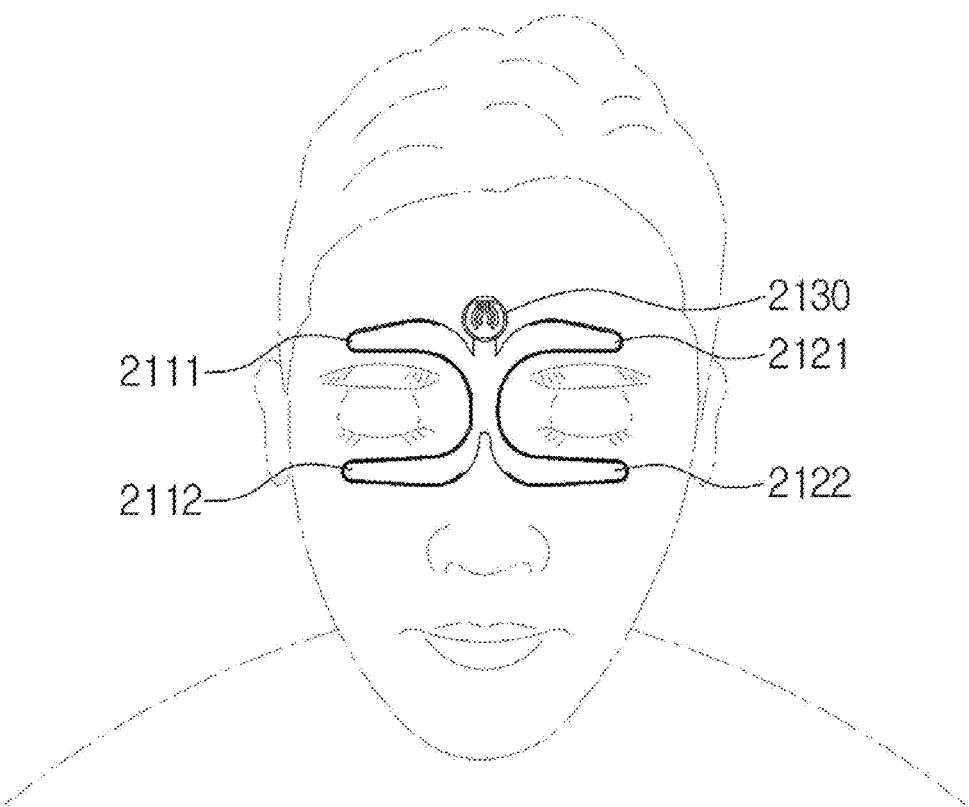
FIG. 8 is a view showing a state of attaching a multichannel unit of a multichannel stimulation system for regenerating damaged corneal nerves according to another embodiment of the present invention in an area close to the eyes of a person.
Figure 9:
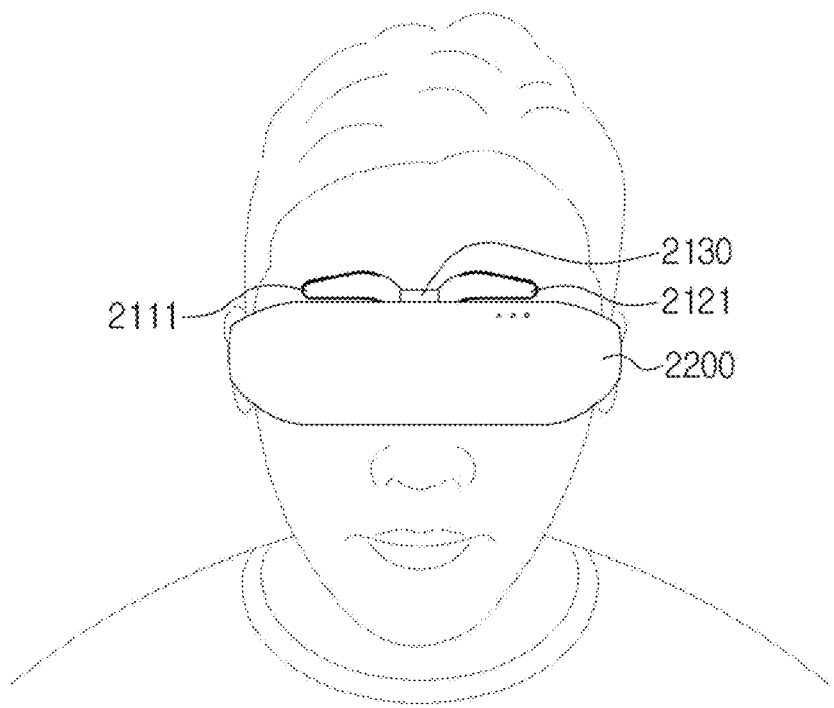
FIG. 9 is a view showing a state of attaching a multichannel unit and a stimulation signal module of a multichannel stimulation system for regenerating damaged corneal nerves according to another embodiment of the present invention in an area close to the eyes of a person.
Figure 10:
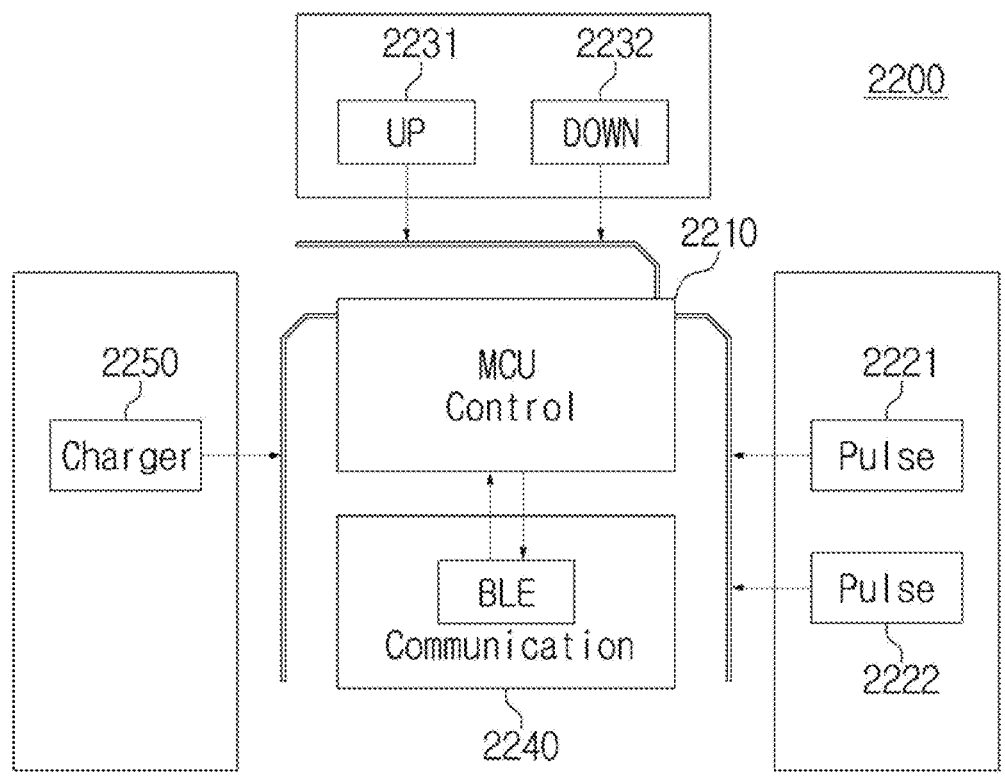
FIG. 10 is a block diagram showing a stimulation signal module of a multichannel stimulation system for regenerating damaged corneal nerves according to another embodiment of the present invention.
Figure 11:
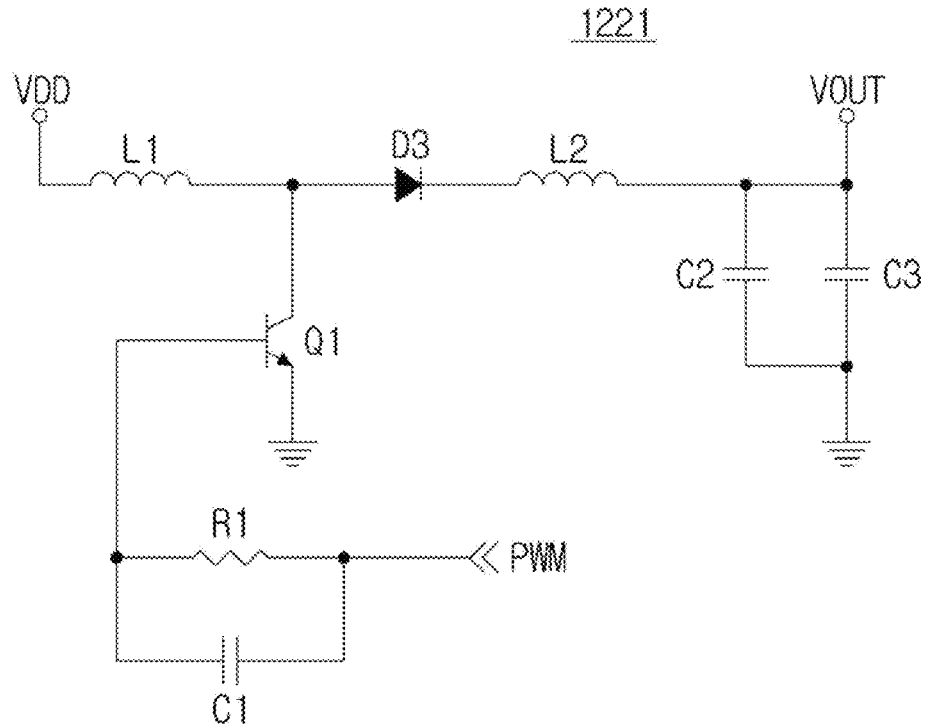
FIG. 11 is a voltage control circuit diagram according to pressure recovery of an up button or a down button employed in a stimulation signal module of a multichannel stimulation system for regenerating damaged corneal nerves according to another embodiment of the present invention.
Figure 12:
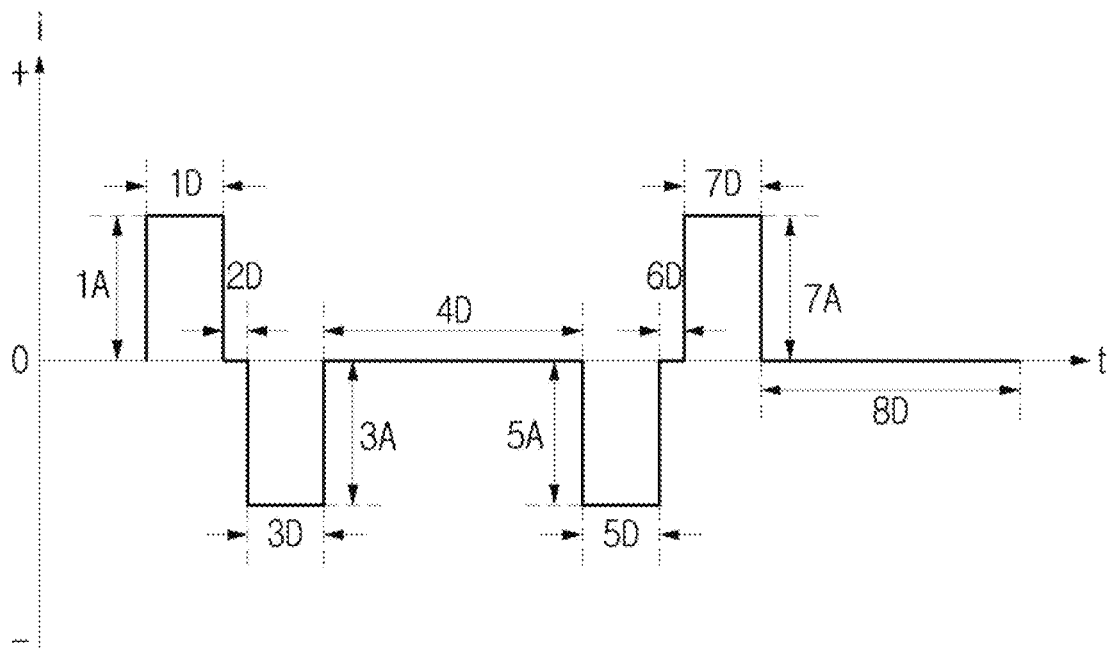
FIG. 12 is a view showing an electric pulse signal provided by a stimulation signal module of a multichannel stimulation system for regenerating damaged corneal nerves according to another embodiment of the present invention.

FIG. 7 is a view showing a multichannel unit of a multichannel stimulation system for regenerating damaged corneal nerves according to another embodiment of the present invention, FIG. 8 is a view showing a state of attaching a multichannel unit of a multichannel stimulation system for regenerating damaged corneal nerves according to another embodiment of the present invention in an area close to the eyes of a person, FIG. 9 is a view showing a state of attaching a multichannel unit and a stimulation signal module of a multichannel stimulation system for regenerating damaged corneal nerves according to another embodiment of the present invention in an area close to the eyes of a person, FIG. 10 is a block diagram showing a stimulation signal module of a multichannel stimulation system for regenerating damaged corneal nerves according to another embodiment of the present invention, FIG. 11 is a voltage control circuit diagram according to pressure recovery of an up button or a down button employed in a stimulation signal module of a multichannel stimulation system for regenerating damaged corneal nerves according to another embodiment of the present invention, and FIG. 12 is a view showing an electric pulse signal provided by a stimulation signal module of a multichannel stimulation system for regenerating damaged corneal nerves according to another embodiment of the present invention.

As shown in FIGS. 7 and 8, a multichannel unit 2100 of a multichannel stimulation system for regenerating damaged corneal nerves according to another embodiment of the present invention includes a 11-th channel 2111 formed of a conductive material and attached above the left eyebrow to transfer a stimulation signal, a 12-th channel 2112 formed of a conductive material and attached below the left eye to transfer the stimulation signal, a 21-th channel 2121 formed of a conductive material and attached above the right eyebrow to transfer the stimulation signal, a 22-th channel 2122 formed of a conductive material and attached below the right eye to transfer the stimulation signal, and a contactor 2130 formed between the 11-th channel 2111 and the 21-th channel 2121 in one piece to electrically contact with the stimulation signal module. Here, the 11-th channel 2111, the 12-th channel 2112, the 21-th channel 2121, the 22-th channel 2122 and the contactor 2130 may be formed of Ag, AgCl, Au, Pt or stainless steel.

In addition, the stimulation signal module 2200 provides the 11-th channel 2111, the 12-th channel 2112, the 21-th channel 2121, and the 22-th channel 2122 with an electric pulse signal as the stimulation signal and may be worn between the eyes and the nose of a person like wearing goggles as shown in FIG. 9, and a magnet is arranged in each of the contactor 2130 of the multichannel unit 2100 and the stimulation signal module 2200, and when the contactor 2130 of the multichannel unit 2100 and the stimulation signal module 2200 approach each other within a predetermined range, the contactor 2130 of the multichannel unit 2100 and the stimulation signal module 2200 are self-aligned by the attraction force of the magnets.

Meanwhile, as shown in FIG. 10, the stimulation signal module 2200 described above includes stimulation signal providing units 2221 and 2222 for generating a electric pulse signal, a control unit 2210 for controlling the stimulation signal providing units 2221 and 2222, an up button 2231, a down button 2232, a communication unit 2240 communicating with the outside, and a charge unit 2250.

When a pressure is applied to the up button 2231 of the stimulation signal module 2200, the magnitude of the electric pulse signal is increased in proportion to the number of times of applying the pressure to the up button 2231, and when a pressure is applied to the down button 2232 of the stimulation signal module 2200, the magnitude of the electric pulse signal is decreased in inverse proportion to the number of times of applying the pressure to the down button 2232.

Specifically, when a pressure is applied to the up button 2231, the stimulation signal module 2200 controls to increase the magnitude of the electric pulse signal by adjusting the number of pulses of a pulse width modulation (PWM) signal in proportion to the number of times of applying the pressure to the up button 2231, and when a pressure is applied to the down button 2232, the stimulation signal module 2200 controls to decrease the magnitude of the electric pulse signal by adjusting the number of pulses of the pulse width modulation (PWM) signal in inverse proportion to the number of times of applying the pressure to the down button 2232.

For example, when the number of times of applying pressure to the up button 2231 is three, as shown in FIG. 11, three pulse width modulation (PWM) signals are transferred to the transistor Q1, and the transistor Q1 is turned on during the three pulse width modulation (PWM) signals, and therefore, the voltage boosted by the inductor L1 is charged in the capacitors C2 and C3 in proportion to the change of current which flows during the three pulse width modulation (PWM) signals. Accordingly, since the boosted voltage is charged in the capacitors C2 and C3 in proportion to the number of pulse width modulation (PWM) signals, it may be controlled to increase the magnitude of the electric pulse signal in proportion to the number of times of applying the pressure to the up button 2231 and to decrease the magnitude of the electric pulse signal in inverse proportion to the number of times of applying the pressure to the down button 2232.

As shown in FIG. 12, the electric pulse signal is configured of a positive electric pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

The fourth duration time 4D of the electric pulse signal is 5 to 2,000 times of the second duration time 2D of the electric pulse signal, and the eighth duration time 8D of the electric pulse signal is 5 to 2,000 times of the sixth duration time 6D of the electric pulse signal.

For example, when the second duration time 2D of the electric pulse signal is 5 μs, the fourth duration time 4D of the electric pulse signal is 25 to 10,000 μs, and when the sixth duration time 6D of the electric pulse signal is 5 μs, the eighth duration time 8D of the electric pulse signal is 25 to 10,000 μs.

In addition, magnitude 1A of the absolute value of the positive current electric pulse signal of the first duration time 1D of the electric pulse signal is equal to magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is equal to magnitude 7A of the absolute value of the positive current electric pulse signal of the seventh duration time 7D of the electric pulse signal.

Meanwhile, magnitude 1A of the absolute value of the positive current electric pulse signal of the first duration time 1D of the electric pulse signal is 2 to 15 times of magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is 2 to 15 times of magnitude 7A of the absolute value of the positive current electric pulse signal of the seventh duration time 7D of the electric pulse signal.

For example, the electric pulse signal is configured to be in a charge-balanced state by configuring the absolute value of the positive current electric pulse signal of the first duration time 1D to be 2 to 15 mA when the absolute value of the negative current electric pulse signal of the third duration time 3D is 1 mA during the equal first duration time 1D and third duration time 3D, and the absolute value of the negative current electric pulse signal of the fifth duration time 5D to be 2 to 15 mA when the absolute value of the positive current electric pulse signal of the seventh duration time 7D is 1 mA during the equal fifth duration time 5D and seventh duration time 7D.

In addition, the length of the first duration time 1D of the electric pulse signal is equal to the length of the third duration time 3D of the electric pulse signal, and the length of the fifth duration time 5D of the electric pulse signal is equal to the length of the seventh duration time 7D of the electric pulse signal.

Meanwhile, the length of the first duration time 1D of the electric pulse signal is 2 to 15 times of the length of the third duration time 3D of the electric pulse signal, and the length of the fifth duration time 5D of the electric pulse signal is 2 to 15 times of the length of the seventh duration time 7D of the electric pulse signal.

For example, the electric pulse signal is configured to be in a charge-balanced state by configuring the first duration time 1D to be 20 to 300 μs when magnitude 1A of the absolute value of the positive current electric pulse signal of the first duration time 1D is equal to magnitude 3A of the absolute value of the negative current electric pulse signal of the third duration time 3D and the length of the third duration time 3D is 10 μs, and the fifth duration time 5D to be 20 to 300 μs when magnitude 5A of the absolute value of the negative current electric pulse signal of the fifth duration time 5D is equal to magnitude 7A of the absolute value of the positive current electric pulse signal of the seventh duration time 7D and the length of the seventh duration time 7D is 10 μs.

Meanwhile, the stimulation signal module 2200 provides the 11-th channel 2111 with the electric pulse signal of the first duration time 1D and the electric pulse signal of the seventh duration time 7D, provides the 12-th channel 2112 with the electric pulse signal of the third duration time 3D and the electric pulse signal of the fifth duration time 5D, provides the 21-th channel 2121 with the electric pulse signal of the first duration time 1D and the electric pulse signal of the seventh duration time 7D, and provides the 22-th channel 2122 with the electric pulse signal of the third duration time 3D and the electric pulse signal of the fifth duration time 5D. That is, the stimulation signal module 2200 provides the same electric pulse signal to the 11-th channel 2111 and the 21-th channel 2121, and provides the same electric pulse signal to the 12-th channel 2112 and the 22-th channel 2122.

Hereinafter, an experiment result of treating damaged corneal nerves using a multichannel stimulation system for regenerating damaged corneal nerves according to the embodiments of the present invention will be described with reference to FIGS. 13 and 14.

Figure 13:
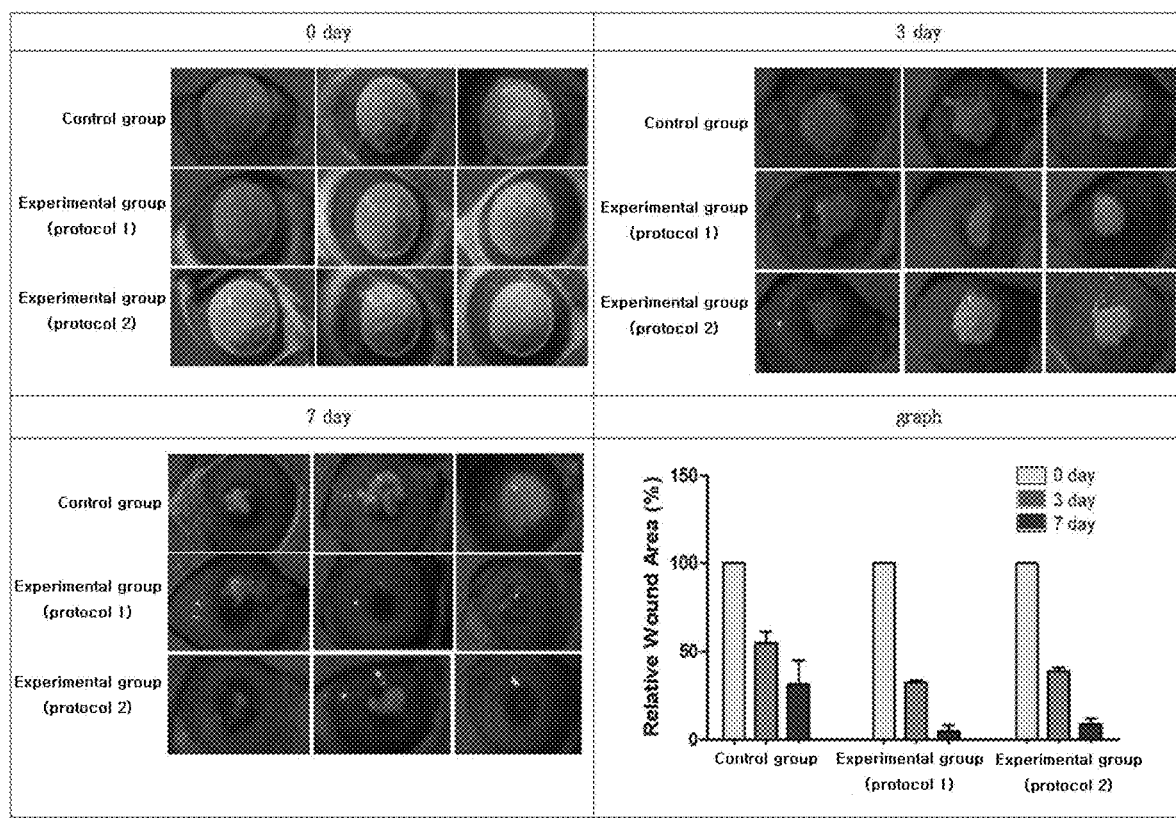
FIG. 13 is a view showing pictures of measuring a degree of treatment of epithelial cells of a damaged cornea after 0 days, 3 days, and 7 days are elapsed while treating the damaged cornea using a multichannel stimulation system for regenerating damaged corneal nerves according to an embodiment of the present invention.

FIG. 13 is a view showing pictures of measuring a degree of treatment of epithelial cells of a damaged cornea after 0 days, 3 days, and 7 days are elapsed while treating the damaged cornea using a multichannel stimulation system for regenerating damaged corneal nerves according to an embodiment of the present invention. Here, a control group measures a damaged cornea of a patient, who has undergone vision correction surgery of cutting part of the cornea, after the patient has a normal treatment for the cornea (e.g., antibiotic administration), a first protocol experimental group measures the damaged cornea while treating the damaged cornea nerves with an electric pulse signal of 20 Hz using a multichannel stimulation system for regenerating damaged cornea nerves according to the embodiments of the present invention, in addition to the normal treatment (e.g., antibiotic administration) for the cornea of a patient who has undergone vision correction surgery of cutting part of the cornea, and a second protocol experimental group measures the damaged cornea while treating the damaged cornea nerves with an electric pulse signal of 2 Hz using a multichannel stimulation system for regenerating damaged cornea nerves according to the embodiments of the present invention, in addition to the normal treatment (e.g., antibiotic administration) for the cornea of the patient who has undergone vision correction surgery of cutting part of the cornea.

As shown in FIG. 13, during the 0-th day, there is no difference between the control group, the first experimental group and the second experimental group, and after three days are elapsed, 54% of the relative damaged area of the control group remain, 32% of the relative damaged area of the first protocol experimental group remain, and 39% of the relative damaged area of the second protocol experimental group remain.

Meanwhile, after seven days are elapsed, 31% of the relative damaged area of the control group remain, 4.7% of the relative damaged area of the first protocol experimental group remain, and 9.0% of the relative damaged area of the second protocol experimental group remain.

Figure 14:
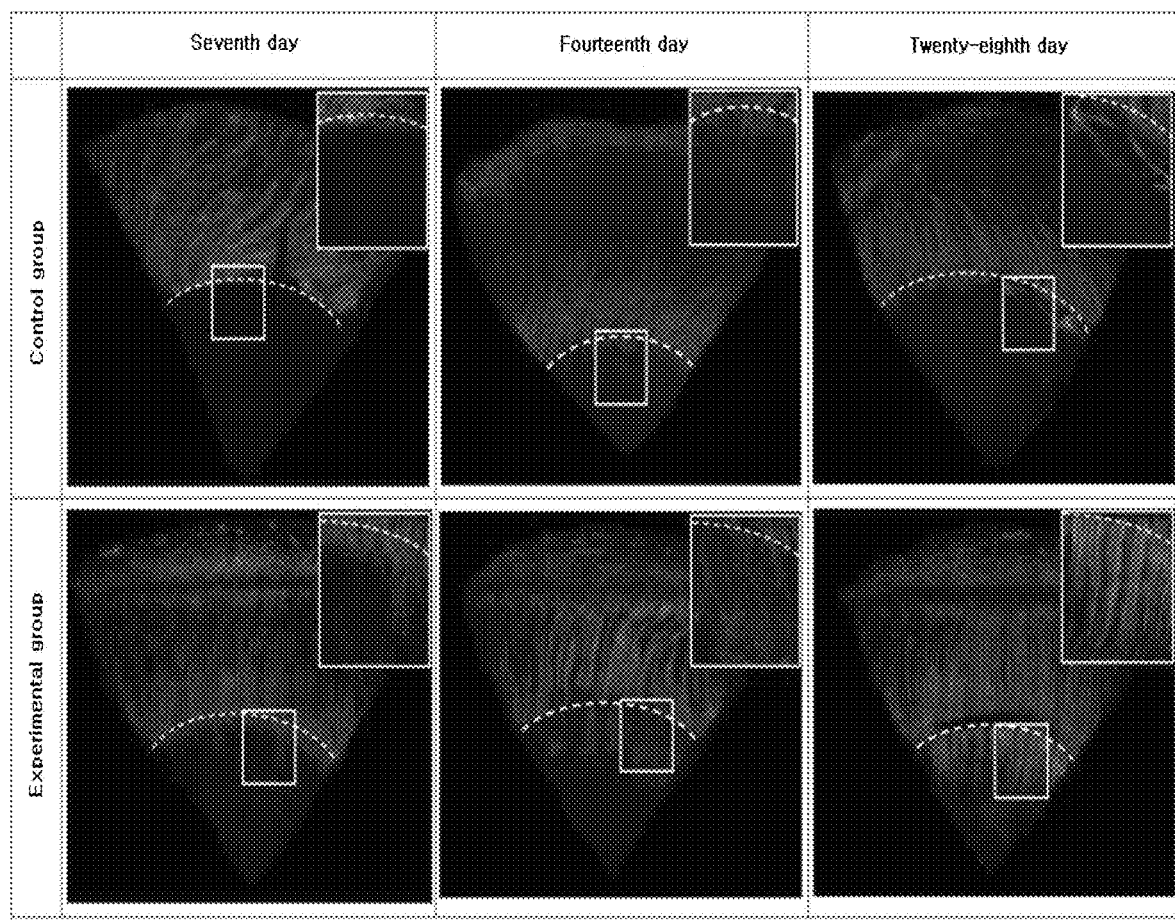
FIG. 14 is a view showing pictures of measuring a degree of regeneration of nerve cells of a damaged cornea using a confocal microscope after 1 week, 2 weeks, and 4 weeks are elapsed while treating the damaged cornea using a multichannel stimulation system for regenerating damaged corneal nerves according to an embodiment of the present invention.

FIG. 14 is a view showing pictures of measuring a degree of regeneration of nerve cells of a damaged cornea using a confocal microscope after 1 week, 2 weeks, and 4 weeks are elapsed while treating the damaged cornea using a multichannel stimulation system for regenerating damaged corneal nerves according to an embodiment of the present invention. Here, a control group measures a degree of regeneration of the nerve cells of a damaged cornea of a patient, who has undergone vision correction surgery of cutting part of the cornea, after the patient has a normal treatment (e.g., antibiotic administration) for the cornea, and an experimental group measures a degree of regeneration of the nerve cells of the damaged cornea while treating the damaged cornea nerves using a multichannel stimulation system for regenerating damaged cornea nerves according to the embodiments of the present invention, in addition to the normal treatment (e.g., antibiotic administration) for the cornea of the patient who has undergone vision correction surgery of cutting part of the cornea.

As shown in FIG. 14, it is understood that the nerve cells of the damaged cornea are regenerated more actively in the experimental groups, compared with the control group, as time is elapsed more.

The multichannel stimulation system for regenerating damaged corneal nerves according to the embodiments of the present invention may effectively regenerate damaged corneal nerves by applying an electric pulse signal as a stimulation signal through multiple channels attached in a plurality of areas close to the eyes.

Although the present invention has been described and shown in relation to the preferred embodiments for illustrating the principle of the present invention, the present invention is not limited to the configuration and operation as is shown and described.

Rather, those skilled in the art may fully understand that the present invention can be diversely changed and modified without departing from the spirit and scope of the appended claims.

Accordingly, all proper changes, modifications and equivalents should be regarded as being included in the scope of the present invention.

What is claimed is:

1. A multichannel stimulation system for regenerating damaged corneal nerves, the system comprising:
   a multichannel unit including a first channel formed of a conductive material and attached between an area above a left eye and a left eyebrow to transfer a stimulation signal, and a second channel formed of a conductive material and attached between an area above a right eye and a right eyebrow to transfer the stimulation signal; and
   a stimulation signal module for providing the first channel and the second channel with an electric pulse signal as the stimulation signal, wherein
   the multichannel unit includes a contactor formed between the first channel and the second channel in one piece to electrically contact with the stimulation signal module, and the electric pulse signal is configured of a positive current pulse signal during a first duration time, a zero current electric pulse signal during a second duration time following the first duration time, a negative current pulse signal during a third duration time following the second duration time, a zero current electric pulse signal during a fourth duration time following the third duration time, a negative current pulse signal during a fifth duration time following the fourth duration time, a zero current electric pulse signal during a sixth duration time following the fifth duration time, a positive current pulse signal during a seventh duration time following the sixth duration time, and a zero current electric pulse signal during an eighth duration time following the seventh duration time, and a length of the first duration time of the electric pulse signal is 2 to 15 times of a length of the third duration time of the electric pulse signal, and a length of the fifth duration time of the electric pulse signal is 2 to 15 times of a length of the seventh duration time of the electric pulse signal.

2. The system according to claim 1, wherein a magnet is arranged in each of the contactor of the multichannel unit and the stimulation signal module, and when the contactor of the multichannel unit and the stimulation signal module approach each other within a predetermined range, the contactor of the multichannel unit and the stimulation signal module are self-aligned by an attraction force of the arranged magnets.

3. The system according to claim 1, wherein when a pressure is applied to an up button of the stimulation signal module, magnitude of the electric pulse signal is increased in proportion to the number of times of applying the pressure to the up button, and when a pressure is applied to the down button of the stimulation signal module, magnitude of the electric pulse signal is decreased in inverse proportion to the number of times of applying the pressure to the down button.

4. The system according to claim 3, wherein when a pressure is applied to the up button, the stimulation signal module controls to increase the magnitude of the electric pulse signal by adjusting the number of pulses of a pulse width modulation signal in proportion to the number of times of applying the pressure to the up button, and when a pressure is applied to the down button, the stimulation signal module controls to decrease the magnitude of the electric pulse signal by adjusting the number of pulses of the pulse width modulation signal in inverse proportion to the number of times of applying the pressure to the down button.

5. The system according to claim 1, wherein the fourth duration time of the electric pulse signal is 5 to 2,000 times of the second duration time of the electric pulse signal.

6. The system according to claim 1, wherein the eighth duration time of the electric pulse signal is 5 to 2,000 times of the sixth duration time of the electric pulse signal.

7. The system according to claim 1, wherein magnitude of an absolute value of the positive current electric pulse signal of the first duration time of the electric pulse signal is equal to magnitude of an absolute value of the negative current electric pulse signal of the third duration time of the electric pulse signal, and magnitude of an absolute value of the negative current electric pulse signal of the fifth duration time of the electric pulse signal is equal to magnitude of an absolute value of the positive current electric pulse signal of the seventh duration time of the electric pulse signal.

8. The system according to claim 1, wherein magnitude of an absolute value of the positive current electric pulse signal of the first duration time of the electric pulse signal is 2 to 15 times of magnitude of an absolute value of the negative current electric pulse signal of the third duration time of the electric pulse signal, and magnitude of an absolute value of the negative current electric pulse signal of the fifth duration time of the electric pulse signal is 2 to 15 times of magnitude of an absolute value of the positive current electric pulse signal of the seventh duration time of the electric pulse signal.

9. The system according to claim 8, wherein the electric pulse signal is in a charge-balanced state.

10. The system according to claim 1, wherein the electric pulse signal is in a charge-balanced state.

11. The system according to claim 1, wherein the stimulation signal module provides the first channel with the electric pulse signal of the first duration time and the electric pulse signal of the seventh duration time, and provides the second channel with the electric pulse signal of the third duration time and the electric pulse signal of the fifth duration time.

12. A multichannel stimulation system for regenerating damaged corneal nerves, the system comprising:
a multichannel unit including a 11-th channel formed of a conductive material and attached above a left eyebrow to transfer a stimulation signal, a 12-th channel formed of a conductive material and attached below a left eye to transfer the stimulation signal, a 21-th channel formed of a conductive material and attached above a right eyebrow to transfer the stimulation signal, and a 22-th channel formed of a conductive material and attached below a right eye to transfer the stimulation signal; and
a stimulation signal module for providing the 11-th channel, the 12-th channel, the 21-th channel, and the 22-th channel with an electric pulse signal as the stimulation signal, wherein
the multichannel unit includes a contactor formed between the 11-th channel and the 21-th channel in one piece to electrically contact with the stimulation signal module, and the electric pulse signal is configured of a positive current pulse signal during a first duration time, a zero current electric pulse signal during a second duration time following the first duration time, a negative current pulse signal during a third duration time following the second duration time, a zero current electric pulse signal during a fourth duration time following the third duration time, a negative current pulse signal during a fifth duration time following the fourth duration time, a zero current electric pulse signal during a sixth duration time following the fifth duration time, a positive current pulse signal during a seventh duration time following the sixth duration time, and a zero current electric pulse signal during an eighth duration time following the seventh duration time, and a length of the first duration time of the electric pulse signal is 2 to 15 times of a length of the third duration time of the electric pulse signal, and a length of the fifth duration time of the electric pulse signal is 2 to 15 times of a length of the seventh duration time of the electric pulse signal.

13. The system according to claim 12, wherein a magnet is arranged in each of the contactor of the multichannel unit and the stimulation signal module, and when the contactor of the multichannel unit and the stimulation signal module approach each other within a predetermined range, the contactor of the multichannel unit and the stimulation signal module are self-aligned by an attraction force of the arranged magnets.

14. The system according to claim 12, wherein when a pressure is applied to an up button of the stimulation signal module, magnitude of the electric pulse signal is increased in proportion to the number of times of applying the pressure to the up button, and when a pressure is applied to the down button of the stimulation signal module, magnitude of the electric pulse signal is decreased in inverse proportion to the number of times of applying the pressure to the down button.

15. The system according to claim 14, wherein when a pressure is applied to the up button, the stimulation signal module controls to increase the magnitude of the electric pulse signal by adjusting the number of pulses of a pulse width modulation signal in proportion to the number of times of applying the pressure to the up button, and when a pressure is applied to the down button, the stimulation signal module controls to decrease the magnitude of the electric pulse signal by adjusting the number of pulses of the pulse width modulation signal in inverse proportion to the number of times of applying the pressure to the down button.

16. The system according to claim 12, wherein the fourth duration time of the electric pulse signal is 5 to 2,000 times of the second duration time of the electric pulse signal.

17. The system according to claim 12, wherein the eighth duration time of the electric pulse signal is 5 to 2,000 times of the sixth duration time of the electric pulse signal.

18. The system according to claim 12, wherein magnitude of an absolute value of the positive current electric pulse signal of the first duration time of the electric pulse signal is equal to magnitude of an absolute value of the negative current electric pulse signal of the third duration time of the electric pulse signal, and magnitude of an absolute value of the negative current electric pulse signal of the fifth duration time of the electric pulse signal is equal to magnitude of an absolute value of the positive current electric pulse signal of the seventh duration time of the electric pulse signal.

19. The system according to claim 12, wherein magnitude of an absolute value of the positive current electric pulse signal of the first duration time of the electric pulse signal is 2 to 15 times of magnitude of an absolute value of the negative current electric pulse signal of the third duration time of the electric pulse signal, and magnitude of an absolute value of the negative current electric pulse signal of the fifth duration time of the electric pulse signal is 2 to 15 times of magnitude of an absolute value of the positive current electric pulse signal of the seventh duration time of the electric pulse signal.

20. The system according to claim 19, wherein the electric pulse signal is in a charge-balanced state.

21. The system according to claim 12, wherein the electric pulse signal is in a charge-balanced state.

22. The system according to claim 12, wherein the stimulation signal module provides the 11-th channel with the electric pulse signal of the first duration time and the electric pulse signal of the seventh duration time, provides the 12-th channel with the electric pulse signal of the third duration time and the electric pulse signal of the fifth duration time, provides the 21-th channel with the electric pulse signal of the first duration time and the electric pulse signal of the seventh duration time, and provides the 22-th channel with the electric pulse signal of the third duration time and the electric pulse signal of the fifth duration time.

* * * * *